United States Patent [19]
Joulain et al.

[11] Patent Number: 5,411,728
[45] Date of Patent: May 2, 1995

[54] USE OF DERIVATIVES OF 6,6-DIMETHYL-2-ACYLCYCLOHEX-4-EN-1,3-DIONES IN THE SUN PROTECTION SECTOR OF THE COSMETICS INDUSTRY, PREPARATIONS CONTAINING THESE DERIVATIVES, NOVEL DERIVATIVE AND PROCESS FOR THE PRODUCTION THEREOF

[75] Inventors: Daniel Joulain, Grasse; Philippe Racine, Magagnosc, both of France

[73] Assignee: Robertet S.A., Grasse, France

[21] Appl. No.: 204,432

[22] Filed: Mar. 2, 1994

[30] Foreign Application Priority Data

Mar. 3, 1993 [FR] France ................. 93 02734
Mar. 3, 1993 [FR] France ................. 93 02735

[51] Int. Cl.⁶ .............................................. A61K 7/42
[52] U.S. Cl. ........................................ 424/59; 568/377
[58] Field of Search ................ 568/377, 378; 424/59

[56] References Cited

U.S. PATENT DOCUMENTS

| | | | |
|---|---|---|---|
| 2,898,374 | 8/1959 | Riedl | 568/377 |
| 4,202,840 | 5/1980 | Gray et al. | 568/377 |
| 5,131,945 | 7/1992 | Bissinger et al. | 568/377 |

FOREIGN PATENT DOCUMENTS

| | | | |
|---|---|---|---|
| 2663848 | 1/1992 | France. | |
| 911289 | 2/1991 | WIPO | 568/377 |

OTHER PUBLICATIONS

Hellyer, Aust. J. Chem, vol. 21, pp. 2825–2828 (1968).
Baigent et al., Chem. Abst., vol. 82 #73198y (1975).
Graham et al., Biochemical Pharmacology, vol. 19, pp. 759–768 (1970).
Patent Abstracts of Japan, vol. 16, No. 528 (C–1001) of Japanese Patent No. A–04 198 131 (Takeda Chem Ind) Jul. 17, 1992 Abstract.
Karlsruhe, Germany, Fishier Chemical Abstracts vol. 75, No. 115854, Abstract taken from S.T.N. Database Server.
Karlsruhe, Germany, Fishier Chemical Abstracts vol. 70, No. 14318, Abstract taken from S.T.N. Database Server.
Sture Forsen "Molecular orbital calculations of some enolised di–and triketones. I. Energies and equilibrium properities." Arkiv Foer Kemi. vol. 20, No. 1, 1962 (Stockholm, Sweden) pp. 1–23.
Lowry, J. B. "A New Constituent of Biogenetic, Pharmacological and Historical Interests from *Melaleuca cajeputi* Oil." Nature vol. 241, 1973 (London, Great Britain) pp. 61–62.

*Primary Examiner*—James H. Reamer
*Attorney, Agent, or Firm*—Browdy and Neimark

[57] ABSTRACT

Use of derivatives of 6,6-dimethyl-2-acylcyclohex-4-en-1,3-diones in the sun protection sector of the cosmetics industry and preparations containing these derivatives, novel derivative and process for the production thereof.

Use of a 6,6-dimethyl-2-acylcyclohex-4-en-1,3-dione derivative of the formula (I)

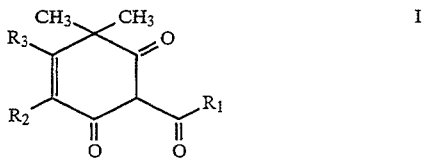

in which $R_1$ is a $C_1$–$C_6$ alkyl radical, $R_2$ is a hydrogen atom or a $C_1$–$C_6$ alkyl radical, $R_3$ is a hydrogen atom, a hydroxy radical or a $C_1$–$C_6$ alkoxy radical as a sunscreen, preparations containing this derivative, novel derivative and process for the production thereof.

19 Claims, No Drawings

USE OF DERIVATIVES OF 6,6-DIMETHYL-2-ACYLCYCLOHEX-4-EN-1,3-DIONES IN THE SUN PROTECTION SECTOR OF THE COSMETICS INDUSTRY, PREPARATIONS CONTAINING THESE DERIVATIVES, NOVEL DERIVATIVE AND PROCESS FOR THE PRODUCTION THEREOF

The present invention relates to the use of 6,6-dimethyl-2-acylcyclohex-4-en-1,3-diones in the sun protection sector of the cosmetics industry, to preparations containing these substances, to a novel derivative of 6,6-dimethyl-2-acylcyclohex-4-en-1,3-dione and to a process for the production thereof.

Whether intended to provide total or partial protection from solar radiation, sun protection products such as sun creams, milks, lotions or sticks for application to the lips all contain one or more sunscreens.

These protective sunscreens are primarily synthetic in origin and are used for the selective absorption of a well defined band of the spectrum of solar ultraviolet radiation. There are thus sunscreens which absorb either ultraviolet B radiation or short or long wave ultraviolet A radiation.

In fact, until recently it was thought that ultraviolet B radiation of the 290 to 320 nm band of the spectrum was the principal cause of sunburn, although it stimulated the tanning response, while ultraviolet radiation of the 320 to 400 nm band was responsible for skin burning and the irritation reactions leading to the formation of melanin with tanning.

For this reason, the great majority of cosmetic sunscreens currently in use absorb only ultraviolet B radiation.

An example of this type of screen for ultraviolet B radiation which may be mentioned is 2-ethylhexyl 4-methoxycinnamate, which is widely used in the cosmetics sector.

Nonetheless, since the part played by ultraviolet A radiation in the appearance of skin cancers has come to be recognised, it has proved necessary to use screens specifically for ultraviolet A radiation in conjunction with sunscreens specifically for ultraviolet B radiation.

Dibenzoylmethane derivatives which absorb ultraviolet A radiation in the 350 nm range are generally used as ultraviolet A screens.

To date, no sunscreen has yet been proposed which is by itself capable of absorbing not only ultraviolet B radiation but also a very significant band of the ultraviolet A spectrum.

The sunscreens used nowadays are selective screens either for ultraviolet A radiations and very faintly for ultraviolet B radiations, or for ultraviolet B radiations and very faintly for ultraviolet A radiations.

The applicant was surprised to discover that certain derivatives of the 6,6-dimethyl-2-acylcyclohex-4-en-1,3-dione family were capable not only of absorbing ultraviolet B radiation, but also a very significant part of ultraviolet A radiation.

These derivatives are members of the family fulfilling the formula (I)

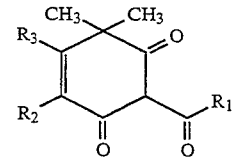

in which $R_1$ is $C_1$ to $C_6$ alkyl radical, $R_2$ is a hydrogen atom or an alkyl radical, $R_3$ is a hydrogen atom, a hydroxy radical or an alkoxy radical.

Members of this family which may be mentioned by way of example are 4,6,6-trimethyl-5-methoxy-2-acetylcyclohex-4-en-1,3-dione which has in particular an absorption maximum at 320 nm, 6,6-dimethyl-5-methoxy-2-isobutyrylcyclohex-4-en-1,3-dione which also has one of its absorption maxima at 322 nm, together with 4,6,6-trimethyl-5-methoxy-2-isobutyrylcyclohex-4-en-1,3-dione, one of the absorption maxima of which is located at 324 nm.

The present invention consequently provides the use of a 6,6-dimethyl-2-acylcyclohex-4-en-1,3-dione of the formula (I)

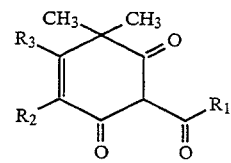

in which $R_1$ is a $C_1$–$C_6$ alkyl radical, $R_2$ is a hydrogen atom or a $C_1$–$C_6$ alkyl radical, $R_3$ is a hydrogen atom, a hydroxy radical or a $C_1$–$C_6$ alkoxy radical as an active principle in cosmetics and in particular as a sunscreen.

In formula (I) and hereafter, a $C_1$–$C_6$ alkyl radical is taken to be a linear or branched radical, for example the methyl, ethyl, n-propyl, methylethyl, n-butyl or n-hexyl, 1,1-dimethylethyl radical; a $C_1$–$C_6$ alkoxy radical is taken to be a linear or branched radical, for example methoxy, ethoxy or n-propoxy.

Certain members of this family of derivatives occur in nature. The following may, in particular, be mentioned:

4,6,6-trimethyl-5-methoxy-2-acetylcyclohex-4-en-1,3-dione (in which $R_1$ and $R_2$ are thus methyl radicals and $R_3$ a methoxy radical in formula (I)), extracted from the leaves of *Melaleuca cajeputi*, a tree of the Myrtaceae family which grows in particular on the Malay Peninsula and on the island of Sumatra in Indonesia;

4,6,6-trimethyl-5-hydroxy-2-n-butyrylcyclohex-4-en-1,3-dione, also known as fraginol (in which $R_1$ is thus a propyl radical, $R_2$ a methyl radical and $R_3$ a hydroxy radical in formula (I)), extracted from *Dryopteris fragrans* (L. M. Molodozhnikova et al., Khim.-Farm. Zh., 1971, 5, 32);

4,6,6-trimethyl-5-methoxy-2-isobutyrylcyclohex-4-en-1,3-dione, also known as tasmanone, (in which $R_1$ is thus an isopropyl radical, $R_2$ a methyl radical and $R_3$ a methoxy radical), which is present in *Eucalyptus tasmanica* (R. O. Hellyet et al., Australian Journal of Chemistry, 1956, 9, 238);

6,6-dimethyl-5-methoxy-2-isobutyrylcyclohex-4-en-1,3-dione, also known as agglomerone (in which $R_1$ is thus an isopropyl radical, $R_2$ is hydrogen and $R_3$ is a methoxy radical in formula (I)), extracted from the essential oils of *Eucalyptus agglomerata* and *Eucalyptus McKieana* (R.O. Hellyet et al., Australian Journal of Chemistry, 1964, 17, 1418);

6,6-dimethyl-2-isobutyrylcyclohex-4-en-1,3-dione, known as xanthostemone, a demethylated analogue of agglomerone, extracted from *Xanthostemon appositifolius* (A. J. Birch et al., Australian Journal of Chemistry, 1956, 9, 238).

As previously stated, currently used sunscreens are essentially of synthetic origin. Replacing them with natural substances proves to be particularly advantageous for use as sunscreen because, since a sunscreen is by definition applied to the body, users are becoming increasingly keen to use natural substances.

The family of derivatives fulfilling formula (I), in which $R_1$ is a $C_1$ to $C_6$ alkyl radical, $R_2$ is a hydrogen atom or an alkyl radical, $R_3$ is a hydrogen atom, a hydroxy radical or an alkoxy radical, may be incorporated into sun protection preparations such as total sunblock or high protection sun creams as a sunscreen.

These preparations may also be milks, lotions, sticks for application to the lips or corresponding gels.

The present invention consequently also provides cosmetic preparations containing at least one sunscreen, characterised in that these preparations contain as sunscreen at least one derivative of 6,6-dimethyl-2-acylcyclohex-4-en-1,3-dione of formula (I), in which $R_1$ is a $C_1$–$C_6$ alkyl radical, $R_2$ is a hydrogen atom or a $C_1$–$C_6$ alkyl radical, $R_3$ is a hydrogen atom, a hydroxy radical or a $C_1$–$C_6$ alkoxy radical.

Advantageously, $R_3$ in formula (I) is an alkoxy radical and preferably a methoxy radical for use as a sunscreen in the preparations containing the sunscreen.

Also advantageous the use in which the preparations are characterised in that $R_1$ is a methyl or isopropyl radical, $R_2$ is a hydrogen atom or a methyl radical, $R_3$ is a methoxy radical.

Preferably, one of the following derivatives of the formula I will be chosen for use as a sunscreen or in a corresponding preparation:

4,6,6-trimethyl-5-methoxy-2-acetylcyclohex-4-en-1,3-dione, 4,6,6-trimethyl-5-hydroxy-2-n-butyrylcyclohex-4-en-1,3-dione, 4,6,6-trimethyl-5-methoxy-2-isobutyrylcyclohex-4-en-1,3-dione, 6,6-dimethyl-5-methoxy-2-isobutyrylcyclohex-4-en-1,3-dione and 6,6-dimethyl-2-isobutyrylcyclohex-4-en-1,3-dione.

It should moreover be noted that the derivatives according to the present invention which are subject to keto-enol tautomerism may be used in any of their tautomeric forms.

Sture Forsén theorised a certain number of formulae of di- and triketone derivatives, for which he drew the formulae and also, theoretically, calculated a certain number of total $\pi$ electron energy and displacement values. Included among these theorised formulae, published in Arkiv for kemi, Vol. 20, n° 1, 1962, is 4,6,6-trimethyl-5-methoxy-2-acetylcyclohex-4-en-1,3-dione above. No constant was determined practically for this product, nor is a process for its preparation stated.

4,6,6-trimethyl-5-methoxy-2-acetylcyclohex-4-en-1,3-dione must be considered to be a novel natural product. The present invention consequently also provides 4,6,6-trimethyl-5-methoxy-2-acetylcyclohex-4-en-1,3-dione fulfilling the detailed formula II

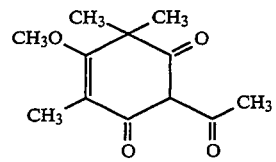

4,6,6-trimethyl-5-methoxy-2-acetylcyclohex-4-en-1,3-dione is subject to keto-enol tautomerism; in nature, it would exist in its two enol tautomeric forms (IIa) and (IIb), at prototropic equilibrium in the proportions 65.3% (IIa) and 34.7% (IIb):

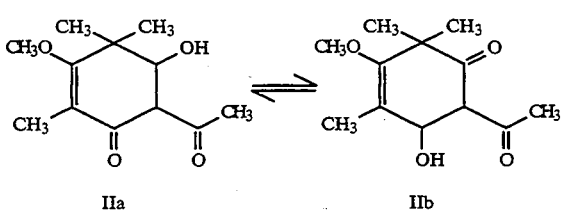

In the remainder of this text, formula (II) and its written form will be used as a "shorthand" term designating 4,6,6-trimethyl-5-methoxy-2-acetylcyclohex-4-en-1,3-dione in any of its tautomeric forms, in particular forms (IIa) and (IIb).

The present invention thus also provides 4,6,6-trimethyl-5-methoxy-2-acetylcyclohex-4-en-1,3-dione of the formula (II), in particular in its tautomeric forms of the formulae (IIa) and (IIb).

The above-mentioned preferred derivative is in particular in its isolated form, particularly in a substantially pure form.

The present application also provides a process for obtaining 4,6,6-trimethyl-5-methoxy-2-acetylcyclohex-4-en-1,3-dione, characterised in that it consists in:

(a) adjusting the pH of a solution of alkali enolates of formula (II) in such a manner as to liberate the corresponding enols;

(b) isolating the said enols by extraction with a solvent, preferably dichloromethane and (c) optionally purifying the said enols by fractional distillation under reduced pressure.

The above solution of alkali enolates may be prepared as follows:

(d) foliage of *Melaleuca cajeputi* is subjected, if fresh or dry, to steam distillation or, if partially dried, to solvent extraction;

(e) the product obtained from stage (d), dissolved in a solvent, is extracted with an alkali carbonate.

Advantageously, the solvent used in stages (d) and (e) above of the process is tert.-butyl methyl ether, ethyl acetate or, preferably, hexane.

The extraction temperature in stage (d) will advantageously be selected between 40° C. and 60° C.

The alkali carbonate in stage (e) is preferably sodium carbonate.

The pH of stage (a) is also preferably adjusted to between 6 and 7, advantageously with an acid, preferably inorganic, such as hydrochloric acid or phosphoric acid.

Since 4,6,6-trimethyl-5-methoxy-2-acetylcyclohex-4-en-1,3-dione also has very good antibacterial and antifungal activity, the present invention also provides the use of 4,6,6-trimethyl-5-methoxy-2-acetylcyclohex-4- en-1,3-dione as an antibacterial agent and antifungal agent respectively.

4,6,6-trimethyl-5-methoxy-2-acetylcyclohex-4-en-1,3-dione may also be incorporated as a medicinal active ingredient, in particular as an antibacterial or antifungal agent, in cosmetic preparations, such as deodorants or other personal hygiene products, or in pharmaceutical preparations.

The present invention thus also provides any cosmetic preparations not containing a sunscreen, together with pharmaceutical preparations characterised in that they contain 4,6,6-trimethyl-5-methoxy-2-acetylcyclohex-4-en-1,3-dione as active ingredient.

4,6,6-trimethyl-5-methoxy-2-acetylcyclohex-4-en-1,3-dione is in particular used in both the preventive and curative treatment of conditions, such as candidiasis and other fungal conditions, related to the microbes against which it is active.

These pharmaceutical or cosmetic preparations may, for example, be pasty or liquid and occur in the presentations commonly used for topical application, such as for example creams or gels; they are prepared using customary methods. The active ingredient or ingredients may be incorporated into the excipients customarily used in these preparations, such as cocoa butter, aqueous or non-aqueous vehicles, animal or vegetable fats, paraffin derivatives, glycols, various wetting, dispersing or emulsifying agents, preservatives.

The following examples serve to illustrate the present invention without, however, restricting it.

EXAMPLE 1

Sun cream

A high-protection sun cream was prepared containing 4,6,6-trimethyl-5-methoxy-2-acetylcyclohex-4-en-1,3-dione as the active ingredient and an oil-in-water emulsion as the excipient containing:
fatty esters,
liquid paraffin,
a carboxyvinyl polymer,
imidazolidinylurea,
a hypoallergenic tested fragrance.

The active ingredient constitutes 1 to 3% of the entire preparation.

By way of comparison, the following table shows the absorbance coefficients of the active ingredient of the above preparation and of 2-ethylhexyl 4-methylcinnamate, which is a screen for ultraviolet B radiation widely used in the cosmetics sector.

These coefficients are, on the one hand, those corresponding to the respective absorption maxima of each substance and, on the other, those corresponding to the wavelength 350 nm for each of the sunscreens.

The values were obtained from an ultraviolet spectrum, the solvent used being methanol.

| Substance | ε max | ε 350 nm |
|---|---|---|
| 4,6,6-trimethyl-5-methoxy-2-acetylcyclohex-4-en-1,3-dione (λ max = 320 nm) | 480 | 370 |
| 2-ethylhexyl 4-methoxycinnamate (λ max = 310 nm) | 607 | 42.6 |

It is clear that at 350 nm, the wavelength at which ultraviolet A selective screens of the dibenzoylmethane type are active, the absorbance coefficient of 4,6,6-trimethyl-5-methoxy-2-acetylcyclohex-4-en-1,3-dione is 8.7 times greater than that of the conventional ultraviolet B screen under the same conditions.

Moreover, the performance of 4,6,6-trimethyl-5-methoxy-2-acetylcyclohex-4-en-1,3-dione as an ultraviolet B screen is very attractive when compared with the performance of the conventional ultraviolet B selective screen.

EXAMPLE 2

Preparation of 4,6,6-trimethyl-5-methoxy-2-acetylcyclohex-4-en-1,3-dione from the essential oil extracted from the leaves of *Melaleuca cajeputi*

Stage A:

45 kg of *Melaleuca cajeputi* leaves are introduced into a double-bottomed, stainless steel still with a capacity of 300 liters. The contents are subjected to steam distillation for 6 hours. 327 g of dark yellow essential oil are collected (yield: 0.72%).

Stage B:

462 g of essential oil as obtained above is dissolved in 1 liter of hexane. This solution is extracted 8 times in succession with 500 ml of 10% aqueous sodium carbonate solution. The carbonate extracts are combined and used as they are in the following stage.

Stage C:

The carbonate extracts obtained above are in turn shaken out twice with 250 ml of hexane in order to remove any neutral organic substances. The pH of the aqueous phase is adjusted to approximately 6.5 by adding a sufficient quantity of 50% hydrochloric acid.

The aqueous phase is then extracted three times with 500 ml of dichloromethane. The organic phases are combined and the solvent evaporated off, finally producing 141 g of a yellow crude product. This product is distilled in a Vigreux fractionating column 15 cm in height and 130 g of light yellow distillate are collected in the form of a mobile liquid, boiling at 133° C. at a pressure of 0.67 kPa. Purity is estimated to be 99.9% minimum by gas chromatography. Density at 20° C. in relation to water taken at 20° C. is 1.152 and the refractive index at 20° C. is 1.546.

The infrared spectrum of 4,6,6-trimethyl-5-methoxy-2-acetylcyclohex-4-en-1,3-dione has intense characteristic bands at 1663 $cm^{-1}$, 1640 $cm^{-1}$, 1540 $cm^{-1}$, 1465 $cm^{-1}$ and 1135 $cm^{-1}$.

The ultraviolet spectrum in methanol has absorption maxima at 242 nm and 320 nm.

The absorbance coefficients are 10940 and 6030 respectively.

Table 1 below relates to the NMR spectrum of the $^1H$ proton. The spectrum was obtained in deuterated chloroform at 400 MHz. The chemical shifts δ are expressed in parts per million in relation to TMS.

It will be noted that all the peaks are singlets and that the proton spectrum allows the two enol tautomeric forms (Ia) and (Ib) to be distinguished within the mixture obtained using the process described above by means of their chemical shifts.

TABLE 1

| Radical | (Ia) δ (ppm) | (Ib) δ (ppm) |
|---|---|---|
| $CH_3$—O | 3.92 | 3.84 |
| $CH_3$—C(=O)— | 2.58 | 2.67 |

TABLE 1-continued

| Radical | (Ia) δ (ppm) | (Ib) δ (ppm) |
|---|---|---|
| CH₃—C=C< | 1.94 | 1.88 |
| (CH₃)₂C< | 1.30 | 1.42 |
| —O—H | approx. 18.95 | approx. 18.15 |

The same distinction may be made with the $^{13}$C NMR spectrum performed at 161 MHz in deuterated chloroform and shown in table 2 below.

The carbon atoms were numbered with reference to the following formula:

TABLE 2

| Carbon atom | (Ia) δ (ppm) | (Ib) δ (ppm) |
|---|---|---|
| C-1 | 197.7 (a) | 197.6 (a) |
| C-2 | 107.6 | 109.9 |
| C-3 | 190.6 | 185.9 |
| C-4 | 112.4 | 118.4 |
| C-5 | 177.4 | 170.9 |
| C-6 | 50.6 | 45.4 |
| C-7 | 10.3 (b) | 9.9 (b) |
| C-8 | 62.6 | 62.3 |
| C-9 | 24.7 (c) | 24.7 (c) |
| C-10 | 24.6 (c) | 24.6 (c) |
| C-11 | 201.6 | 204.4 |
| C-12 | 28.4 | 29.7 |

It will be noted here that, since the values marked (a), (b) and (c) are identical or very similar, it is not possible to assign them with any certainty to specific carbon atoms: these values are interchangeable.

Table 3 illustrates the mass spectrum of the mixture of tautomeric forms (Ia) and (Ib) in 4,6,6-trimethyl-5-methoxy-2-acetylcyclohex-4-en-1,3-dione.

The table shows the mass to charge ratios m/z of the various peaks, together with the relative intensity of each of the corresponding peaks.

TABLE 3

| m/z | % |
|---|---|
| 43 | 100 |
| 81 | 61 |
| 224 | 39 |
| 41 | 34 |
| 209 | 31 |
| 139 | 25 |
| 192 | 25 |
| 125 | 23 |
| 67 | 20 |
| 69 | 19 |

EXAMPLE 3

Another particularly advantageous application of 4,6,6-trimethyl-5-methoxy-2-acetylcyclohex-4-en-1,3-dione is as an antibacterial or antifungal agent.

Indeed, as shown in table 5, the antibacterial activity of 4,6,6-trimethyl-5-methoxy-2-acetylcyclohex-4-en-1,3-dione was tested in vitro on various microorganisms at concentrations of 0.1% and 0.2% in a culture medium, in this case agar-agar.

Activity was evaluated on a scale from 0 (no activity) to 5 (complete inhibition of microbial growth).

TABLE 5

| Microorganisms | Concentration 0.1% | 0.2% |
|---|---|---|
| *Staphylococcus epidermidis* | 2 | 5 |
| *Corynebacterium xerosis* | 2 | |
| *Escherichia coli* | 1 | 3 |
| *Pseudomonas aeruginosa* | 1 | 2 |
| *Candida albicans* | 5 | |
| *Penicillium sp.* | 5 | |
| *Aspergillus glaucus* | 5 | |
| *Fusarium soleri* | 5 | |

These results confirm that 4,6,6-trimethyl-5-methoxy-2-acetylcyclohex-4-en-1,3-dione has good antimicrobial activity, particularly against bacteria and fungi, and may thus advantageously be used for this purpose.

In particular, thanks to its activity against underarm flora, combined with its low volatility (its vapour pressure at 25° C. being some 1.5 μm of mercury), 4,6,6-trimethyl-5-methoxy-2-acetylcyclohex-4-en-1,3-dione is an effective deodorant.

It may thus be used in a cosmetic preparation such as a deodorant in the following proportions by weight:

EXAMPLE 4

Cosmetic preparation

A deodorant was prepared using the following formula:

| 96° ethanol | 72% |
|---|---|
| 4,6,6-trimethyl-5-methoxy-2-acetylcyclohex-4-en-1,3-dione | 0.2% |
| demineralised water | 27.8% |

This preparation provides good deodorant activity, lasting on average 12 hours for the majority of subjects.

Such a deodorant shares the objects set for the present invention in that it consists of substances which are all natural.

EXAMPLE 5

Variant of example 2.

Partially dried *Melaleuca cajeputi* foliage is extracted with hexane at approximately 50° C. using a static extractor as customarily used in the perfume raw materials industry, and the product obtained, dissolved in hexane, is then extracted with sodium carbonate. The process is then continued as described in stage (c) above in order to obtain the expected product.

EXAMPLE 6

Cosmetic preparation

A cream of the following composition by weight was prepared:

| Part A | |
|---|---|
| Wheat germ oil | 0.5 |
| Glyceryl stearate ceteareth 20 | 7.0 |
| PEG 30 glyceryl stearate | 5.0 |
| Cetyl alcohol | 1.0 |
| Propylparaben | 0.1 |
| BHT | 0.05 |
| Liquid paraffin | 6.0 |
| Substance (I) | 3.0 |
| Part B | |
| Demineralised water | 60.0 |
| Methylparaben | 0.15 |
| Carbopol 940 | 0.2 |
| Glycerol | 5.0 |
| Part C | |
| Demineralised water | 11.84 |
| Triethanolamine | 0.16 |

Procedure

The ingredients of the fatty phase (A) are mixed together in a stainless steel melting kettle by raising the temperature to 80° C.

In another melting kettle, the water is-heated to 80° C. and the propylparaben and carbopol are drizzled in (while the mixture is vigorously stirred), and then the glycerol is poured in.

The fatty phase (60° C.) is slowly added to the aqueous phase (B) (60° C.) while the mixture is stirred (avoiding entrainment of air).

When the emulsion begins to thicken, phase (C) and then, if desired, a fragrance in a quantity of 0.2–0.5% is slowly poured in and the mixture is homogenised.

We claim:

1. Cosmetic preparation containing at least one sunscreen and at least one non-aqueous vehicle, containing as active ingredient a sun-shielding effective concentration of at least one derivative of 6,6-dimethyl-2-acylcyclohex-4-en-1,3-dione of the formula (I)

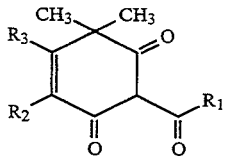

in which $R_1$ is a $C_1$–$C_6$ alkyl radical, $R_2$ is a hydrogen atom or a $C_1$–$C_6$ alkyl radical, $R_3$ is a hydrogen atom, a hydroxy radical or a $C_1$–$C_6$ alkoxy radical.

2. Preparation according to claim 1, characterised in that $R_3$ is a $C_1$–$C_6$ alkoxy radical.

3. Preparation according to claim 1, characterised in that $R_3$ is a methoxy radical.

4. Preparation according to claim 1, characterised in that $R_1$ is a methyl or isopropyl radical, $R_2$ is a hydrogen atom or a methyl radical, $R_3$ is a methoxy radical.

5. Preparation according to claim 1, characterised in that the compound of formula I is selected from the group consisting of:
   4,6,6-trimethyl-5-methoxy-2-acetylcyclohex-4-en-1,3-dione,
   4,6,6-trimethyl-5-hydroxy-2-n-butyrylcyclohex-4-en-1,3-dione,
   4,6,6-trimethyl-5-methoxy-2-isobutyrylcyclohex-4-en-1,3-dione,
   6,6-dimethyl-5-methoxy-2-isobutyrylcyclohex-4-en-1,3-dione and
   6,6-dimethyl-2-isobutyrylcyclohex-4-en-1,3-dione.

6. 4,6,6-trimethyl-5-methoxy-2-acetylcyclohex-4-en-1,3-dione of the formula (II):

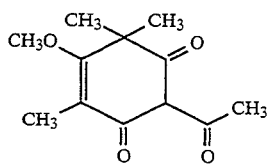

in any one of its various tautomeric forms.

7. A method of shielding the skin from solar radiation comprising applying to the skin a sun-shielding effective amount of a compound derived from 6,6-dimethyl-2-acylcychlohex-4-en-1,3-dione of the formula (I)

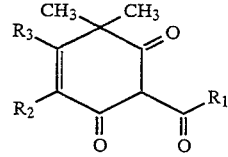

in which $R_1$ is a $C_1$–$C_6$ alkyl radical, $R_2$ is a hydrogen atom or a $C_1$–$C_6$ alkyl radical, $R_3$ is a hydrogen atom, a hydroxy radical or a $C_1$–$C_6$ alkoxy radical, as a sunscreen.

8. A method according to claim 7 wherein $R_3$ is a $C_1$–$C_6$ alkoxy.

9. A method according to claim 7 wherein $R_3$ is a methoxy.

10. A method according to claim 7 wherein $R_1$ is a methyl or isopropyl radical, $R_2$ is a hydrogen atom or a methyl radical, $R_3$ is a methoxy radical.

11. A method according to claim 7 wherein said compound is selected from the group consisting of:
   4,6,6-trimethyl-5-methoxy-2-acetylcyclohex-4-en-1,3-dione
   4,6,6-trimethyl-5-hydroxy-2-butyrylcyclohex-4-en-1,3-dione
   4,6,6-trimethyl-5-methoxy-2-isobutyrylcyclohex-4-en-1,3-dione
   6,6-dimethyl-5-methoxy-2-isobutyrylcyclohex-4-en-1,3-dione, and
   6,6-dimethyl-2-isobutyrylcyclohex-4-en-1,3-dione 12. A cosmetic preparation according to claim 1, wherein said at least one non-aqueous vehicle comprises at least one of an alcohol, glycerol, liquid paraffin, and an oil.

13. A cosmetic preparation according to claim 12 in the form of a cream or gel.

14. A cosmetic preparation according to claim 12 in the form of an emulsion.

15. A cosmetic preparation according to claim 1 containing 1–3% of said active ingredient.

16. In a cosmetic preparation containing a vehicle and a sun-shielding effective concentration of at least one sunscreen, the improvement wherein said at least one sunscreen comprises 4,6,6-trimethyl-5-methoxy-2-acetylcyclohex-4-en-1,3-dione.

17. A cosmetic preparation according to claim 16 in the form of a sunscreen lotion.

18. A cosmetic preparation according to claim 16 in the form of an anti-bacterial/anti-fungal personal hygiene composition.

19. A method of shielding skin from solar radiation according to claim 7 wherein said compound is
   4,6,6-trimethyl-5-methoxy-2-acetylcyclohex-4-en-1,3-dione.

* * * * *